United States Patent [19]
Schmitt et al.

[11] 3,986,998
[45] Oct. 19, 1976

[54] MIXING LIQUID FOR SILICATE CEMENTS

[75] Inventors: Werner Schmitt; Robert Purrmann, both of Starnberg; Peter Jochum; Wolf-Dieter Zahler, both of Hechendorf; Rainer Grimm-Lenz, Seefeld, Upper Bavaria, all of Germany

[73] Assignee: ESPE, Fabrik Pharmazeutischer Praparate GmbH, Germany

[22] Filed: Oct. 10, 1973

[21] Appl. No.: 404,886

Related U.S. Application Data

[63] Continuation-in-part of Ser. No. 213,829, Dec. 29, 1971, abandoned.

[30] Foreign Application Priority Data
Jan. 15, 1971 Germany............................ 2101889

[52] U.S. Cl............................ 260/29.6 WB; 106/35; 260/29.6 H; 260/29.6 S; 260/29.6 M; 260/42
[51] Int. Cl.²......................................... C08L 35/02
[58] Field of Search.................. 260/29.6 H, 29.6 S, 260/29.6 R, 42 R, 29.6 WB, 29.6 M; 106/35

[56] References Cited
UNITED STATES PATENTS

| | | | |
|---|---|---|---|
| 2,227,200 | 12/1940 | Robie............................. | 260/29.6 S |
| 3,238,159 | 3/1966 | DiBenedetti et al............ | 260/29.6 S |
| 3,655,605 | 4/1972 | Smith................................... | 106/35 |
| 3,814,717 | 6/1974 | Wilson et al.................. | 260/29.6 M |

FOREIGN PATENTS OR APPLICATIONS

| | | | |
|---|---|---|---|
| 2,061,513 | 6/1971 | Germany............................. | 106/35 |

*Primary Examiner*—Harold D. Anderson
*Attorney, Agent, or Firm*—Ostrolenk, Faber, Gerb & Soffen

[57] ABSTRACT

Dental cements are prepared by mixing a silicate powder with an aqueous solution of polymers of unsaturated alpha, beta-dicarboxylic acids.

7 Claims, No Drawings

MIXING LIQUID FOR SILICATE CEMENTS

BACKGROUND OF THE INVENTION

This is a continuation-in-part of application Ser. No. 213,829 filed Dec. 29, 1971, now abandoned.

Silicate cements are produced, as known, by the dentist from a two component system: a mixing liquid, generally a buffered aqueous orthophosphoric acid, and as a powder component, an aluminum fluorsilicate glass (see e.g., Materials for the Practicing Dentist, p. 58–60; The C. V. Mosely Co., St. Louis, 1969).

In addition to silicate cements, amalgams and plastics are also used as permanent filling materials. The former, however, are not used for esthetic reasons where they are visible, and the plastics, though they could achieve a certain portion of the market in recent years, still meet great resistance because of the risk of discoloration. Additionally, as a rule, they are harmful to the pulpa, like the ordinary silicate cements, and can therefore only be treated by observing expensive and time-consuming precautions.

There has been no lack of attempts to improve the properties of the silicate cements (see e.g., German Offenlegungsschrift (DOS) 1,802,313 and 1,941,480).

A disadvantage of the silicate cements is that they are harmful to the pulpa and relatively soluble in the mouth region. The former weakness is naturally particularly serious; it necessitates the application of cavity lacquers or underfillings, procedures which are time-consuming and in many cases, unreliable.

The object of the invention is to improve the properties, particularly the physiological compatability of the silicate cements, without reducing the other advantages, particularly their esthetic appearance and the relatively high compressive strength.

SUMMARY OF THE INVENTION

This invention relates to dental cements. More particularly, this invention relates to dental cements prepared by mixing a silicate powder with an aqueous solution of polymers of unsaturated alpha, beta-dicarboxylic acids.

DESCRIPTION OF THE PREFERRED EMBODIMENTS

The object of this invention is achieved by using as a mixing liquid, aqueous solutions of polymers of unsaturated alpha, beta-dicarboxylic acids as a liquid component, instead of the usual phosphoric acid.

As in all cements, the mixing liquid according to the invention is used for a two-component silicate cement.

The liquid component is an aqueous solution of polymers of ethylenically unsaturated alpha, beta-dicarboxylic acids. Preferred are the polymers of unsaturated alpha, beta-dicarboxylic acids with 4 or 5 carbon atoms. Polymaleic acid has proved to be particularly successful, but polyitaconic acid is also suitable. Also useful are copolymers of the two above mentioned acids, as well as their copolymers with other ethylenically unsaturated carboxylic acids, particularly acrylic acid. Polymers of other carboxylic acids, for example, polyacrylic acids, can also be used as an addition to the polycarboxylic acids in an amount of about 0.1 to 50% of said polycarboxylic acids.

The polymeric acids are used in aqueous, at least 20%, solutions. In general, a concentration of 65% will not be exceeded, otherwise gelling might easily occur or the solutions may become too viscous. The preferred concentration range is between 35% and 65%, particularly between 40% and 50%.

The polycarboxylic acids, particularly polymaleic acid, can be easily obtained according to known methods in solid form, for example, by further concentration of concentrated solutions by freeze-drying or by precipitation from aqueous solutions with non-solvents.

The solutions of the polycarboxylic acids should be used with a viscosity of at least 0.5 poise; solutions with viscosities of over 3000 poise, preferably over 600 poise, are generally not suitable, since they are difficult to handle and the stirred cements show a tendency of forming "cobwebs". A preferred viscosity range is between 2 and 200 poise/25° C., particularly between 5 and 100 poise/25° C.

The production of the polyacids used according to the invention is known: (see e.g. DOS 1,944,756; 1,570,708; 1,645,100; German Pat. No. 1,162,083; J. L. Lang et al., J. of Polymer Science, A 1, 1123(1963); C. S. Marvel et al., J. of Organic Chemistry 24, 599 (1959).

The common silicate powders can be used, that is, the inorganic glasses as they are found in commercial silicate cement powders for dental purposes in ground and sifted form in corresponding tooth-like colors (see e.g. Skinner Phillips, The Science of Dental Materials, Fifth Edition, W. B. Saunders Co. (1960) p. 244 ff). The glasses in question can be called aluminum-fluorosilicate-glasses. They are usually produced from mixtures of aluminum-oxide and silica with the addition of fluxes like calcium fluoride or cryolite.

After heating to about 1400° C., the glasses are ground in ball mills and sifted. By adding pigments, tooth-like colors are obtained, preferably powders with different pigment additions are produced to meet all requirements.

The two components, that is, the silicate powder and the polycarboxylic acid solution, are mixed on a support, for example, a glass plate or a block of hardened paper. The setting starts after a few minutes; in the tooth, the mixture will usually harden after 5 minutes at most. Setting times, and, to a certain extent, the strength of the end product are determined partly by the ratio of powder to liquid. As a rule, a weight ratio (powder/liquid) of not less than 1:1 will be selected to achieve a pleasant consistency, and a mixing ratio of 4:1 will not be exceeded. A preferred mixing ratio of powder and liquid is between 1.5:1 and 2.5:1.

An optimum consistency is obtained according to the regulations of American Dental Association specification No. 9, par. 4.3.2.

In recent years, it has become increasingly customary to sell dental-preparations pre-dosed in so-called shaking caps. Liquid and powder are kept in separate compartments and combined immediately before use by suitable devices and subsequently mixed mechanically.

This pre-dosing is also applicable to the mixing liquid according to the invention. In a special embodiment, the system can be divided into silicate-cement powder, solid polydicarboxylic acid and water, instead of the usual division into liquid and powder, that is, in the present case, into silicate cement powder and polydicarboxylic acid solution. This system has the advantage that it makes the dosing more reliable and the mixing easier since the relatively viscous solutions are avoided. In this system, the powder/polymer ratio is 1.5:1 to 20:1 and preferably between 2.3:1 and 12.5:1.

These systems can furthermore be so varied that the solid components, that is, silicate cement powder and polydicarboxylic acid, are premixed and packed pre-dosed as a powder mixture, since the solid substances do not react with each other. The second component is then water, if necessary, with the usual bacteriostatic additions, etc.

The cements produced with the mixing liquid according to the invention, unlike the known silicate cements and filling materials based on plastics, are not harmful to the pulpa. They are esthetically pleasant and thus superior to amalgams. Their solubility is favorable, that is, they are relatively insoluble under mouth conditions.

It could not be expected that the physiological properties of the silicate cements could be improved decisively by the use of aqueous solutions of polymers of unsaturated alpha, beta-dicarboxylic acids without losing the advantages of the silicate cements.

The mixing liquid, according to the invention, can also be used for all other common dental cements.

In the following Examples, the addition of pigments customary for the production of tooth-like colors will not be mentioned specifically, since it corresponds to the state-of-the-art.

EXAMPLE 1

Polymaleic acid, suitable for dental-medical purposes, and produced according to the method of DOS 1,944,756, is mixed with water to a concentration of 48% by weight (the solution has a viscosity of 10.5 poise/25° C.). The powder used is a commercial silicate cement (Syntrex).

The powder and liquid are mixed in a weight ratio of 1.9:1 to obtain a paste that is well suitable for clinical purposes. The paste is introduced in known manner into prepared tooth cavities. The mixture hardens after a few minutes and has, in the set state, a transparency corresponding to the natural tooth.

EXAMPLE 2

The liquid of Example 1 is mixed with the silicate cement powder known under the name Achatit in a powder-liquid ratio of 1.6:1. The mixture yields esthetically pleasant permanent fillings in teeth.

EXAMPLE 3

A silicate cement powder, produced in known manner, which contains per analysis 39.5% $SiO_2$, 28.1% $Al_2O_3$, 6.1% Ca, 15.2% F, 6.6% Na and 4.0% $P_2O_5$, is mixed with the liquid mentioned in Example 1 in a weight ratio of 2.4:1. The cement mixture is particularly suitable for the production of fillings in the molar region and has a high compressive strength.

EXAMPLE 4

A 58% solution of polymaleic acid, produced according to DOS 1,570,708 and by subsequent hydrolysis, is made into a paste with 2.1 parts of the powder of Example 1 and is used as a permanent filling material.

EXAMPLE 5

Polymaleic acid, produced according to DOS 1,645,100, is used as a 47% aqueous solution and mixed with 1.4 parts of the powder of Example 2.

EXAMPLE 6

A 54% aqueous solution of polyitaconic acid, produced according to DOS 1,944,756, is mixed with 2 parts silicate cement powder (Syntrex). The paste is introduced into a tooth cavity and hardens after a few minutes.

EXAMPLE 7

The aqueous solution of polymaleic acid of Example 1 is filled in portions of 80 mg into foil bags consisting of plastic coated aluminum, and sealed. The foil bags are inserted into the cover part of two-component containers as described in DOS 1,910,885. 155 mg of a commercial silicate cement powder are filled into each container part provided as a mixing chamber.

When such a filled capsule is used, as described in DOS 1,910,885, we obtain by means of a mechanical shaking device, a paste of optimum consistency, which is highly suitable for tooth fillings.

COMPARISON TESTS

The comparison tests were carried out according to the regulations of ADA, specification No. 9, par. 4.3. Mixtures of standard consistency were processed and molded bodies were tested for compressive strength.

RESULTS

| Powder | Mixing Liquid | Mixing Ratio | Compressive Strength (kg/sq cm) |
| --- | --- | --- | --- |
| Syntrex | According to invention; Example 1 | 1.9:1 | 1,590 |
| Syntrex | Syntrex | 2.4:1 | 1,620 |
| Achatit | According to invention; Example 2 | 1.6:1 | 1,580 |
| Achatit | Achatit | 2.4:1 | 1,570 |

As it can be seen, the compressive strength is about as good as in the known preparations, while the fillings prepared with the mixing liquid according to the invention, unlike the silicate cements, are completely harmless to the pulpa.

Instead of the polydicarboxylic acids used in the Examples, other polymers of unsaturated alpha, beta-dicarboxylic acids, as well as copolymers, can also be used. Particularly suitable are copolymers of maleic acid and itaconic acid, where the maleic acid portion can be relatively high, e.g., 80 mole percent. Also suitable are copolymers of unsaturated alpha, beta-dicarboxylic acids with unsaturated monocarboxylic acids, particularly acrylic acid or methacrylic acid. Here too, copolymers which have a relatively high content of dicarboxylic acid units deserve preference. Particularly suitable are copolymers which contain primarily maleic acid, in addition to acrylic acid or methacrylic acid, particularly copolymers which contain more than 90 mole percent maleic acid.

Suitable also are polymers or copolymers of the above mentioned type, which contain additionally small amounts, that is, not more than 10 mole percent, of monomers free of carboxyl groups. Particularly suitable are copolymers with methacrylic esters (the ester moiety can be alkyl, preferably 1 to 4 C-atoms), acrylic amide, methacrylic amide, as well as derivatives substituted on nitrogen.

Various changes and modifications can be made in the composition of this invention without departing from the spirit and the scope thereof. The various embodiments of the invention disclosed herein serve to further illustrate the invention, but are not intended to limit it.

We claim:

1. The method of making a dental silicate cement comprising forming a paste by mixing an aluminum fluorosilicate glass powder with an aqueous solution of a solid polymeric material selected from the group consisting of a homopolymer of an ethylenically unsaturated alpha, beta-dicarboxylic acid of 4-5 carbon atoms, a copolymer of said acids with each other, and a copolymer of said acids with less than 10 mole percent of an ethylenically unsaturated monocarboxylic acid, methacrylic ester wherein the ester moiety is alkyl of 1-4 carbon atoms or methacrylic amide, said aqueous solution containing 20-65 weight percent polymer and having a viscosity of 0.5 to 3000 poise at 25° C. and subsequently permitting said paste to harden into a dental silicate cement.

2. The method of claim 1, wherein the aqueous solution contains 35-65 weight percent polymer and the solution has a viscosity of 2 to 200 poise at 25° C.

3. The method of claim 1, wherein the aqueous solution contains 40-50 weight percent polymer and the solution has a viscosity of 5 to 100 poise at 25° C.

4. The method of claim 1, wherein the polymer is polymaleic acid.

5. The method of claim 1, wherein the aqueous solution additionally contains dissolved therein about 0.1-50% based on said polymeric material of solid polyacrylic acid.

6. The method of claim 1, wherein the weight ratio of the silicate powder to mixing liquid is 1.5:1 to 2.5:1.

7. The hardened dental silicate cement made by the method of claim 1.

* * * * *